US010195467B2

(12) United States Patent
Tran et al.

(10) Patent No.: US 10,195,467 B2
(45) Date of Patent: Feb. 5, 2019

(54) ABLATION CATHETER SYSTEM WITH WIRELESS RADIO FREQUENCY TEMPERATURE SENSOR

(71) Applicant: Boston Scientific Scimed, Inc., Maple Grove, MN (US)

(72) Inventors: Binh C. Tran, Minneapolis, MN (US); Greg Paul Carpenter, Centerville, MN (US)

(73) Assignee: Boston Scientific Scimed, Inc., Maple Grove ( * ) Notice: Subject to any disclaimer, the term of this patent is extended or adjusted under 35 U.S.C. 154(b) by 1213 days.

(21) Appl. No.: 14/185,994

(22) Filed: Feb. 21, 2014

(65) Prior Publication Data

US 2014/0236137 A1  Aug. 21, 2014

Related U.S. Application Data

(60) Provisional application No. 61/767,665, filed on Feb. 21, 2013.

(51) Int. Cl.
*A61B 18/18* (2006.01)
*A61N 7/02* (2006.01)
(Continued)

(52) U.S. Cl.
CPC .......... *A61N 7/022* (2013.01); *A61B 18/1492* (2013.01); *A61B 2018/00404* (2013.01);
(Continued)

(58) Field of Classification Search
CPC ...... A61B 18/1492; A61B 2018/00404; A61B 2018/00434; A61B 2018/00511;
(Continued)

(56) References Cited

U.S. PATENT DOCUMENTS 4,102,195 A * 7/1978 Thompson ............. G01K 11/26
374/117
5,154,387 A   10/1992 Trailer
(Continued)

FOREIGN PATENT DOCUMENTS

EP   1690510 A1   8/2006
WO   WO-2008118992 A1   10/2008
(Continued)

OTHER PUBLICATIONS

Hopcroft, M.A., Using the Temperature Dependence of Resonator Quality Factor as a Thermometer, Jul. 2007, American Institute of Physics, Applied Physics Letters 91.*
(Continued)

*Primary Examiner* — Michael Peffley
*Assistant Examiner* — Amanda Zink

(57) ABSTRACT

Disclosed herein, among other things, are methods and apparatus related to ablation catheter systems with wireless temperature sensing. The present subject matter provides an ablation catheter system including an ablation catheter configured to ablate a target zone of tissue and at least one temperature sensitive resonator coupled to the ablation catheter. The resonator is configured to wirelessly emit a signal indicative of a sensed temperature in response to an interrogation signal. The ablation catheter system also includes an external device configured to provide the interrogation signal and to receive and decode the emitted signal from the resonator. The temperature sensitive resonator is configured to be placed proximate to and in thermal conduction with the target zone of tissue and to resonate at a frequency dependent upon a temperature of the resonator when excited by the interrogation signal, in various embodiments.

12 Claims, 9 Drawing Sheets

(51) Int. Cl.
*A61B 18/14* (2006.01)
*A61B 18/00* (2006.01)
*A61N 7/00* (2006.01)

(52) U.S. Cl.
CPC ............ *A61B 2018/00434* (2013.01); *A61B 2018/00511* (2013.01); *A61B 2018/00577* (2013.01); *A61B 2018/00791* (2013.01); *A61N 2007/003* (2013.01)

(58) Field of Classification Search
CPC ........... A61B 2018/00577; A61B 2018/00791; A61N 2007/003; A61N 7/022
See application file for complete search history.

(56) References Cited

U.S. PATENT DOCUMENTS

| | | |
|---|---|---|
| 5,919,188 A | 7/1999 | Shearon et al. |
| 6,053,912 A | 4/2000 | Panescu et al. |
| 6,569,162 B2 | 5/2003 | He |
| 6,602,242 B1 | 8/2003 | Fung et al. |
| 6,640,120 B1 | 10/2003 | Swanson et al. |
| 6,689,128 B2 | 2/2004 | Sliwa, Jr. et al. |
| 6,804,545 B2 | 10/2004 | Fuimaono et al. |
| 6,805,128 B1 | 10/2004 | Pless et al. |
| 7,278,993 B2 | 10/2007 | Kelly et al. |
| 7,387,126 B2 | 6/2008 | Cox et al. |
| 8,221,409 B2 | 7/2012 | Cao et al. |
| 2002/0107511 A1 | 8/2002 | Collins et al. |
| 2003/0004506 A1 | 1/2003 | Messing |
| 2003/0101822 A1* | 6/2003 | Atherton ................. E21B 47/06 73/649 |
| 2004/0092806 A1 | 5/2004 | Sagon et al. |
| 2004/0122494 A1* | 6/2004 | Eggers .................... A61B 18/04 607/103 |
| 2005/0070894 A1 | 3/2005 | McClurken |
| 2007/0043397 A1 | 2/2007 | Ocel et al. |
| 2008/0091193 A1 | 4/2008 | Kauphusman et al. |
| 2008/0161797 A1 | 7/2008 | Wang et al. |
| 2008/0243214 A1* | 10/2008 | Koblish ............... A61B 5/0422 600/374 |
| 2008/0300454 A1 | 12/2008 | Goto |
| 2009/0093810 A1 | 4/2009 | Subramaniam et al. |
| 2010/0331658 A1 | 12/2010 | Kim et al. |
| 2011/0009857 A1 | 1/2011 | Subramaniam et al. |
| 2011/0022041 A1 | 1/2011 | Ingle et al. |
| 2011/0028826 A1 | 2/2011 | Kim et al. |
| 2011/0098696 A1* | 4/2011 | Brannan ................ A61B 18/18 606/33 |
| 2011/0224667 A1 | 9/2011 | Koblish et al. |
| 2012/0277737 A1* | 11/2012 | Curley ................ A61B 18/082 606/33 |
| 2013/0178910 A1* | 7/2013 | Azamian .......... A61B 17/00234 607/33 |

FOREIGN PATENT DOCUMENTS

| | | |
|---|---|---|
| WO | WO-2009048824 A1 | 4/2009 |
| WO | WO-2009048943 A1 | 4/2009 |
| WO | WO-2011008444 A1 | 1/2011 |
| WO | WO-2011008681 A1 | 1/2011 |
| WO | WO-2011115787 A1 | 9/2011 |

OTHER PUBLICATIONS

"U.S. Appl. No. 12/821,459, Non Final Office Action dated Aug. 20, 2012", 20 pgs.
"U.S. Appl. No. 12/821,459, Notice of Allowance dated Dec. 10, 2012", 8 pgs.
"U.S. Appl. No. 12/821,459, Response filed Jun. 11, 2012 to Restriction Requirement dated May 10, 2012", 10 pgs.
"U.S. Appl. No. 12/821,459, Response filed Nov. 20, 2012 to Non Final Office Action dated Aug. 20, 2012", 14 pgs.
"U.S. Appl. No. 12/821,459, Restriction Requirement dated May 10, 2012", 8 pgs.
"U.S. Appl. No. 13/043,301, Preliminary Amendment filed Mar. 8, 2011", 3 pgs.
"International Application Serial No. PCT/US2010/039600, International Search Report dated Nov. 10, 2010", 5 pgs.
"International Application Serial No. PCT/US2010/039600, Invitation to Pay Additional Fee dated Aug. 30, 2010", 6 pgs.
"International Application Serial No. PCT/US2010/039600, Written Opinion dated Nov. 10, 2010", 8 pgs.
"International Application Serial No. PCT/US2010/041677, International Search Report dated Aug. 20, 2010", 4 pgs.
"International Application Serial No. PCT/US2010/041677, Written Opinion dated Aug. 20, 2010", 6 pgs.
"International Application Serial No. PCT/US2011/027591, International Preliminary Report on Patentability dated Sep. 27, 2012", 7 pages.
"International Application Serial No. PCT/US2011/027591, International Search Report dated Jun. 17, 2011", 4 pgs.
"International Application Serial No. PCT/US2011/027591, Written Opinion dated Jun. 17, 2011", 6 pgs.

* cited by examiner

701: EXTERNAL DEVICE SENDS AN RF SIGNAL TO EXCITE THE TEMPERATURE SENSITIVE RESONATOR AND THE RESONATOR "RINGS" IN RESPONSE TO THE EXTERNAL EXCITATION, TRANSMITTING A SIGNAL WITH THE FREQUENCY RELATED TO THE TEMPERATURE OF THE RESONATOR

702: THE EXTERNAL DEVICE, WITH RECEIVE CAPABILITY, RECEIVES THE "RINGING" FROM THE TEMPERATURE SENSITIVE RESONATOR DISPOSED UPON THE ABLATION CATHETER

703: THE EXTERNAL DEVICE IDENTIFIES THE FREQUENCY OF THE "RINGING" AND DETERMINES A TEMPERATURE (OR TEMPERATURE CHANGE) ASSOCIATED WITH THE SIGNAL FREQUENCY

704: THE TEMPERATURE INFORMATION IS TRANSMITTED TO A REAL TIME DISPLAY

FIG. 7

ABLATION CATHETER SYSTEM WITH WIRELESS RADIO FREQUENCY TEMPERATURE SENSOR

CLAIM OF PRIORITY

This application claims the benefit of priority under 35 U.S.C. § 119(e) of U.S. Provisional Patent Application Ser. No. 61/767,665, filed on Feb. 21, 2013, which is herein incorporated by reference in its entirety.

CROSS REFERENCE TO RELATED APPLICATION

This application is related to, commonly assigned, U.S. Patent Application Ser. No. 61/767,671, entitled "ABLATION CATHETER WITH WIRELESS TEMPERATURE SENSOR", filed on Feb. 21, 2013, which is hereby incorporated by reference in its entirety.

TECHNICAL FIELD

This application relates generally to medical devices and, more particularly, to systems and methods related to ablation catheters.

BACKGROUND

Tissue ablation is the destruction of tissue, typically pathologic tissue, with the aim to cure a disease. Ablation has been used in numerous applications. For example, cardiac ablation is one form of treatment for restoring normal conduction in patients with cardiac arrhythmias. The sources of the aberrant pathways are located, and the aberrant tissue is ablated.

Renal sympathetic nerves have been identified as a contributor to hypertension, as patients with hypertension exhibit increased sympathetic activity relating to the kidneys. Ablation of renal nerves is one way of treating hypertension. In radio frequency (RF) ablation, RF energy is directed from the ablation electrode through tissue to ablate the tissue and form a lesion.

Renal denervation and other catheter based ablation applications would benefit from real-time, active monitoring of tissue temperatures in the vicinity of the treatment target. Traditional temperature monitoring techniques that include wires which extend through the length of the catheter to a sensor at the catheter tip can adversely impact catheter performance and can be impractical. For example, the need to include a wire for each sensor would add bulk, stiffness, or diameter to the catheter, affecting its size, maneuverability, and possibly safe use. Conversely, the number of temperature sensors or monitoring points available in a catheter may be limited in order to maintain catheter functional characteristics. Wireless temperature monitoring technology for ablation catheter systems is described herein to mitigate limitations of traditional wired temperature sensors.

SUMMARY

Disclosed herein, among other things, are methods and apparatus related to ablation catheter systems with wireless temperature sensing. The present subject matter provides an ablation catheter system including an ablation catheter configured to ablate a target zone of tissue and at least one temperature sensitive resonator coupled to the ablation catheter. The resonator is configured to wirelessly emit a signal indicative of a sensed temperature in response to an interrogation signal. The ablation catheter system also includes an external device configured to provide the interrogation signal and to receive and decode the emitted signal from the resonator. The temperature sensitive resonator is configured to be placed proximate to and in thermal conduction with the target zone of tissue and to resonate at a frequency dependent upon a temperature of the resonator when excited by the interrogation signal, in various embodiments.

One aspect of the present subject matter provides an ablation catheter system including an ablation catheter and at least one temperature sensitive resonator coupled to the ablation catheter. An external device is configured to generate a first radio frequency (RF) signal to interrogate the resonator and to receive and decode a second RF signal from the resonator in response to being interrogated. The second RF signal is indicative of a temperature sensed by the resonator, in various embodiments.

Another aspect of the present subject matter includes a method of using an ablation catheter. The method includes delivering electrical power, using an external electrical generator, to the ablation catheter to provide an ablation therapy to a target zone of tissue. Various embodiments of the method also include applying a wireless signal to interrogate a temperature sensitive resonator coupled to the ablation catheter. According to various embodiments, interrogating the resonator excites the resonator to emit a signal in response to the interrogating signal, wherein the resonance frequency of the response signal is related to the temperature sensed by the resonator. In various embodiments, the system uses radio frequency electromagnetic signals. According to various embodiments, determining a temperature for the target zone of tissue involves determining the temperature-dependent resonance frequency of the resonator.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates a flow diagram of a method of using an ablation catheter system with wireless temperature sensing, according to various embodiments of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein, among other things, are methods and apparatus related to ablation catheter systems with wireless temperature sensing. The present subject matter provides: an ablation catheter configured to ablate a target zone of tissue; at least one temperature sensitive resonator coupled to the ablation catheter, the resonator configured to wirelessly transmit a signal indicative of a sensed temperature in response to an interrogation signal; and, an external device configured to provide a signal to interrogate the temperature sensitive resonator, and, receive and decode a response signal indicative of a sensed temperature. In various embodiments of the present invention, the system operates using radio frequency (RF) electromagnetic signals. According to various embodiments, the temperature sensitive resonator is configured to sense a temperature in proximity to a vessel wall and/or target ablation zone, and to resonate at a frequency dependent upon the sensed temperature in response to an external interrogation.

Some embodiments ablate renal nerves for the treatment of hypertension. Other types of tissue heating and ablation can be performed using the present systems and methods, without departing from the scope of the present subject matter. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Renal denervation may reduce blood pressure by deactivating these sympathetic nerves, and may be a viable treatment option for many patients with hypertension who do not respond to conventional drugs.

Figure 1:
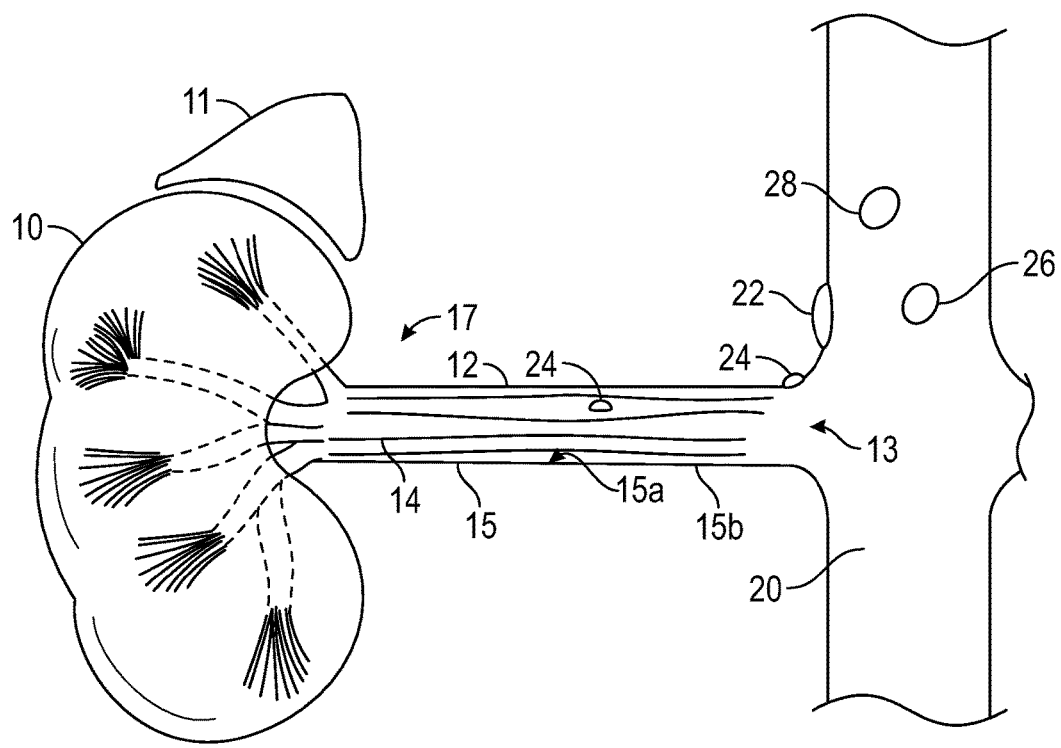
FIG. 1 is an illustration of a kidney and selected renal nerves and vasculature.

FIG. 1 is an illustration of a kidney 10 and renal vasculature including a renal artery 12 branching laterally from the abdominal aorta 20. The right and left kidneys are supplied with blood from the right and left renal arteries that branch from respective right and left lateral surfaces of the abdominal aorta 20. The right and left renal arteries extend from the abdominal aorta 20 to respective renal sinuses proximate the hilum 17 of the kidneys, and branch into segmental arteries and then interlobular arteries within the kidney 10. Also shown in FIG. 1 is the suprarenal gland 11, commonly referred to as the adrenal gland.

The autonomic nervous system of the body controls involuntary actions of the smooth muscles in blood vessels, the digestive system, heart, and glands. The autonomic nervous system includes the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

Figure 2A:
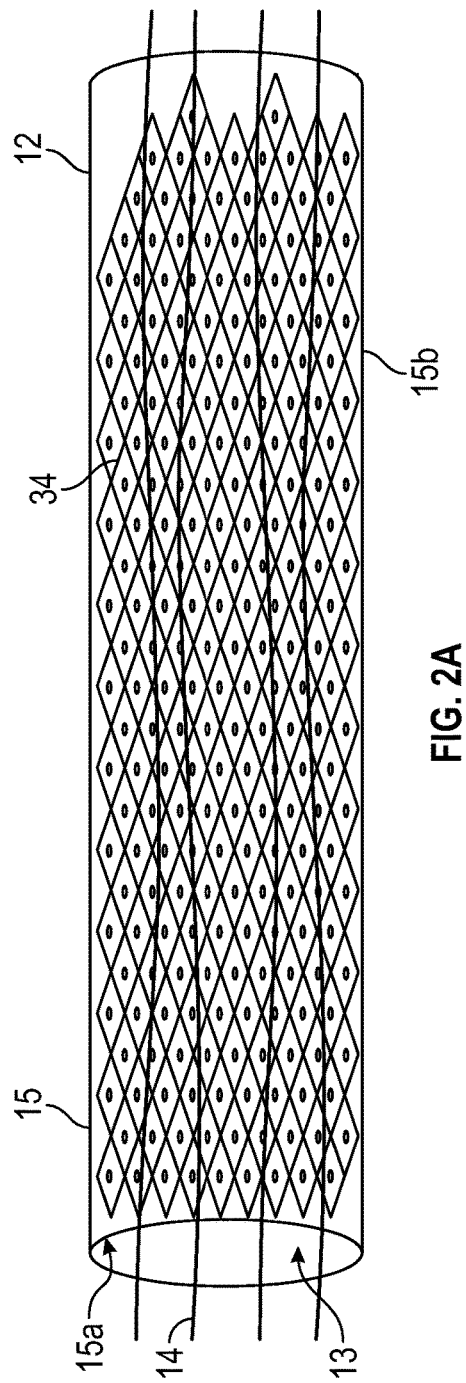
FIGS. 2A-2B illustrate innervation associated with the renal artery.
Figure 2B:
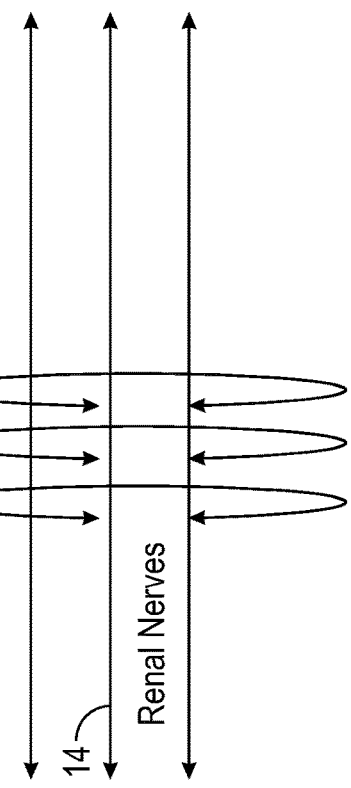

FIGS. 1 and 2A-2B illustrate sympathetic innervation associated with the renal vasculature, primarily innervation of the renal artery 12. Renal nerves 14 innervate the kidneys and ureters. The primary functions of sympathetic nerves associated with the renal vasculature include signaling to and from the kidney, regulation of renal blood flow and pressure, stimulation of renin release, and direct stimulation of water and sodium ion reabsorption.

Most of the nerves innervating the renal vasculature are sympathetic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Nerve fibers from other renal ganglia, such as the renal ganglia 24, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

The renal artery 12 is lined with smooth muscle 34 that controls the diameter of the renal artery lumen 13. The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14. The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
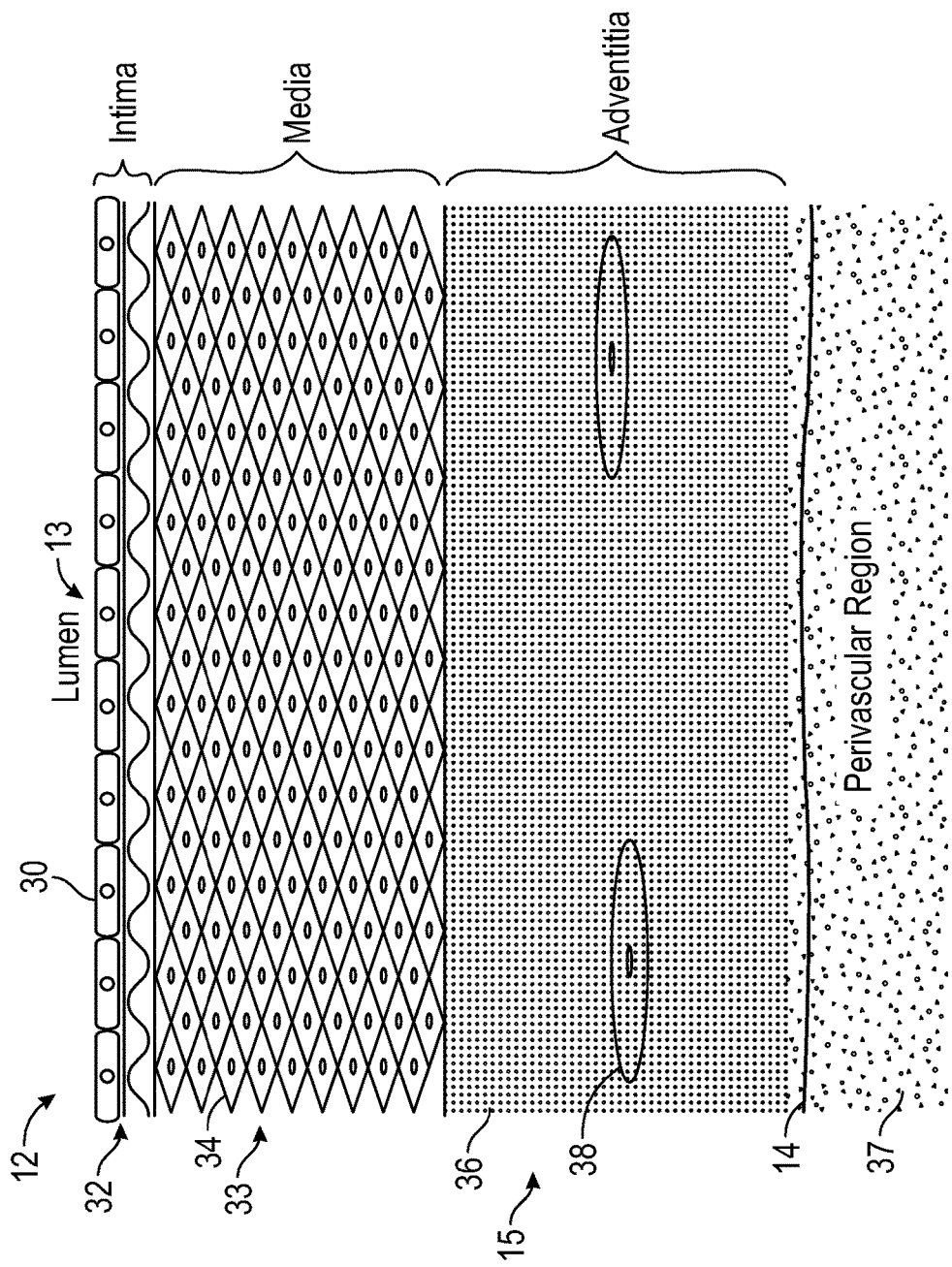
FIGS. 3A-3C illustrate various portions of the renal nerve and artery.

FIG. 3A shows a segment of a longitudinal cross-section through a renal artery, and illustrates various tissue layers of the wall 15 of the renal artery 12. The innermost layer of the renal artery wall 15 is the intima, which is lined with endothelium 30, which is supported by an internal elastic lamina 32. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, including the inner elastic lamina 32.

Adjacent the intima is the media 33, which is the middle layer of the renal artery wall 15. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is largely made up of connective tissue. The adventitia 36 includes fibroblast cells 38 that play an important role in wound healing.

Figure 3B:
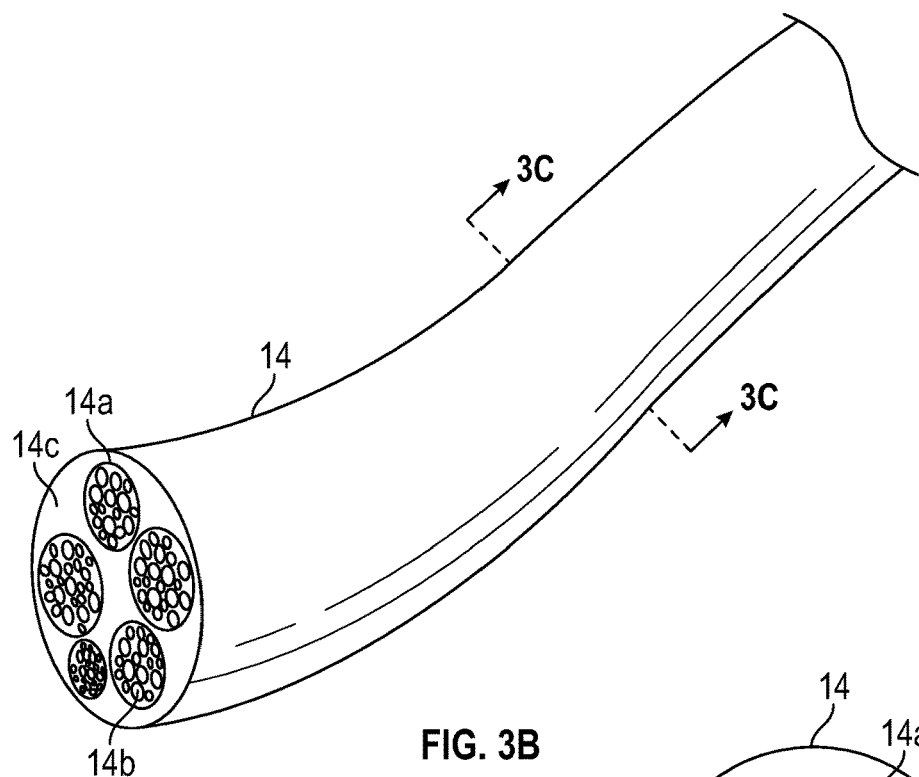
Figure 3C:
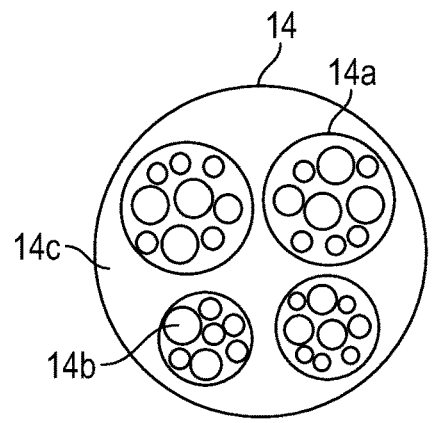

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to innervate the renal artery smooth muscle 34. FIGS. 3B and 3C illustrate the renal nerve 14 in more detail. Bundles 14*a* of nerve fibers 14*b* each comprise axons or dendrites that originate or terminate on cell bodies or neurons located in ganglia or on the spinal cord, or in the brain. Supporting tissue structures 14*c* of the nerve 14 include the endoneurium (surrounding nerve axon fibers), perineurium (surrounds fiber groups to form a fascicle), and epineurium (binds fascicles into nerves), which serve to separate and support nerve fibers 14*b* and bundles 14*a*.

In some embodiments, a treatment apparatus of the disclosure may be implemented to deliver denervation therapy that causes transient and reversible injury to renal nerve fibers 14*b*. In other embodiments, a treatment apparatus of the disclosure may be implemented to deliver denervation therapy that causes more severe injury to renal nerve fibers 14*b*, which may be reversible if the therapy is terminated in a timely manner. In still other embodiments, a treatment apparatus of the disclosure may be implemented to deliver denervation therapy that causes even more severe injury to renal fibers 14*b*, which may be irreversible.

Figure 4:
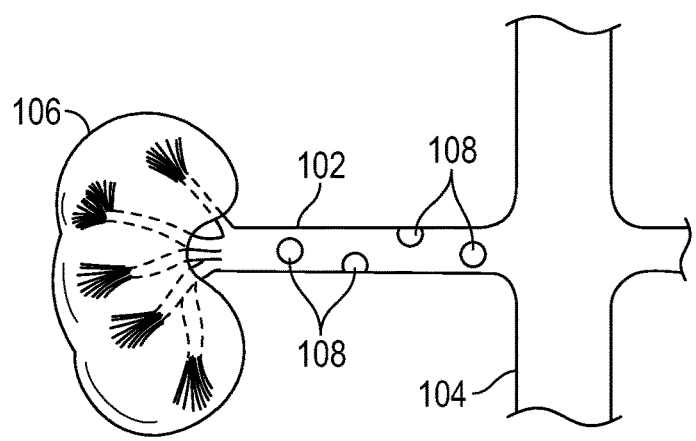
FIG. 4 illustrates ablation sites along the renal artery.

FIG. 4 illustrates ablation sites 108 along the renal artery 102, which connects a kidney 106 to the aorta 104. Ablation of perivascular renal nerves has been used as a treatment for hypertension. RF or ultrasonic (acoustic) energy can be used for renal denervation for treatment of hypertension, in various embodiments. For example, RF or ultrasonic energy can be delivered from a catheter situated in the renal artery to tissues containing a renal nerve, just beyond the vessel wall. Therapy effectiveness may be affected by differences in local anatomy from patient to patient. RF electrodes on catheters placed in the renal artery can be used to ablate the nerves, but with risk of artery wall injury. To control injury to the artery wall, one method is to move the RF electrode to ablate at discrete locations along and around the artery; this can cause local renal artery injury due to the local high temperatures resulting from high current density near the electrodes, but reduces the potential for significant stenotic narrowing of the artery after the ablation procedure. In some approaches, a spiral pattern of ablation spots has been used to ablate the nerves while minimizing injury to the vessel wall. However, reliably positioning the electrode to ensure the desired relative spacing between ablation spots has been difficult, and repeated ablation cycles is also time-consuming. In some cases, it is desirable to independently monitor temperature at each ablation site, to distribute the ablation energy as desired and prevent injury to tissue. Real time temperature monitoring can provide instantaneous feedback useful for adjusting therapy parameters such as power and duration, to ensure treatment effectiveness. However, multipoint temperature monitoring using wired temperature sensors has been impractical due to the increased bulk and stiffness added to the catheter by the separate electrical wires attached to each temperature sensor. An improved system capable of concurrent temperature monitoring and ablation therapy is needed.

Figure 8A:
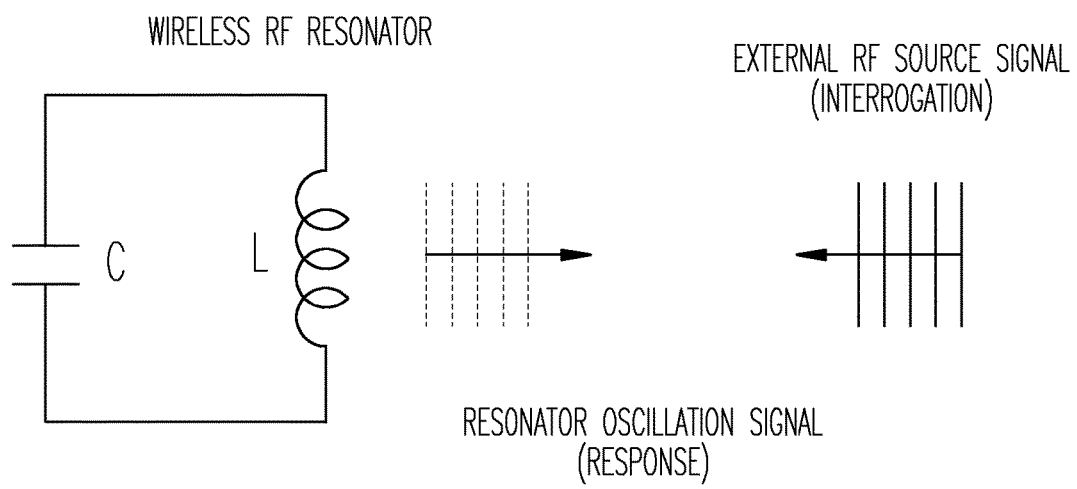
FIGS. 8A-8C illustrate temperature sensitive resonator configurations, according to various embodiments of the present subject matter.
Figure 8B:
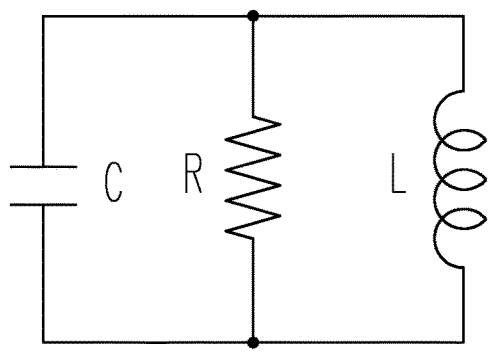
Figure 8C:
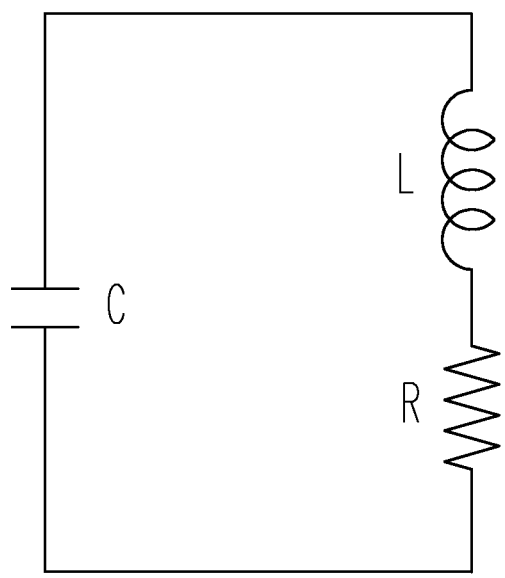

Disclosed herein, among other things, is an ablation catheter system with wireless temperature sensing. In various embodiments the system includes: an ablation catheter configured to ablate a target zone of tissue; at least one temperature sensitive resonator coupled to the ablation catheter, the resonator configured to wirelessly transmit a signal indicative of a sensed temperature in response to an interrogation signal; and, an external device configured to provide a signal to interrogate the temperature sensitive resonator, and, receive and decode a response signal indicative of a sensed temperature. In various embodiments of the present invention, the system uses RF electromagnetic signals. FIG. 8A illustrates the operating principals of a system including a temperature sensitive resonator. An example wireless resonator circuit is constructed from an inductor element (L) and a capacitor element (C). FIGS. 8B and 8C illustrate additional resonator circuit configurations that include a resistor element (R). In one example, when an electromagnetic signal is applied, the electromagnetic (E/M) field couples to the resonator inducing an electric current in the circuit which charges the capacitor. When the external E/M signal is removed, the resonator circuit emits its own E/M signal with frequency of oscillation dictated by the capacitance and inductance of the elements, as the capacitor and inductor interact in a charge/discharge cycle until the energy stored in the capacitor is released. The temperature sensitive resonator is a passive sensor in that it harvests the energy needed for its operation from the E/M signal and does not require a battery. In the present subject matter, temperature sensitive resistor, inductor, and capacitor elements are utilized to develop temperature sensitive resonators that emit E/M signals with temperature dependent resonant frequencies. These signals are received by an external device and the signals are decoded to determine the sensed temperature.

A loop, coil, or spiral of wire is an example of a simple E/M resonator. FIG. 8A illustrates one embodiment of a temperature sensitive resonator comprised of a single loop of coiled wire. A loop of coiled wire has self-inductance and self-capacitance, a product of the loop size and wire to wire spacing, and thereby a natural resonance. In one embodiment, a loop of coiled wire is patterned on a balloon manufactured from a temperature sensitive substrate. In one embodiment, the temperature sensitive substrate experiences temperature changes and the substrate undergoes physical deformation in the form of expansion and contraction. The deformation of the temperature sensitive substrate changes the self-inductance and self-capacitance of the coil loop by changing the wire to wire separation. In another embodiment, the temperature sensitive substrate experiences temperature changes and the substrate undergoes dielectric property changes. The dielectric changes of the temperature sensitive substrate changes the self-capacitance of the coil loop. The resonance frequency of the signal emitted by the resonator changes in accordance with the changes in the inductance and capacitance of the coiled loop.

A loop, coil, or spiral of wire connected to a capacitor is another example of a resonator. FIG. 8B illustrates one embodiment of a temperature sensitive resonator comprised of a single loop of coiled wire connected to a temperature sensitive capacitor. A parallel plate capacitor has a capacitance based on the plate spacing and the dielectric material between the plates. When connected, a coil loop and capacitor have a natural resonance. In one embodiment, a loop of coiled wire is patterned on a substrate and connected to a parallel plate capacitor including a temperature sensitive dielectric substrate. In one embodiment, the temperature sensitive substrate experiences temperature changes and the substrate undergoes physical deformation in the form of expansion and contraction. The deformation of the temperature sensitive substrate changes the capacitance of capacitor by changing the separation between the capacitor plates. In another embodiment, the temperature sensitive substrate experiences temperature changes and the substrate undergoes dielectric property changes. The dielectric changes of the temperature sensitive substrate changes the capacitance of the capacitor. The resonance frequency of the signal emitted by the resonator changes in accordance with the changes in the capacitance.

A loop, coil, or spiral of wire connected to a capacitor and a resistor is yet another example of a resonator. FIG. 8C illustrates one embodiment of a temperature sensitive resonator comprised of a single loop of coiled wire connected to a capacitor and temperature sensitive resistor. A thermistor is an example of a temperature sensitive resistor. When connected, a coiled loop, capacitor, and temperature sensitive resistor have a natural resonance. In one embodiment, a loop of coiled wire is patterned on a substrate and connected to a capacitor and a temperature sensitive resistor. In one embodiment, the temperature sensitive resistor experiences temperature changes and loads the circuit in relation to the temperature change. The resonance frequency of the signal emitted by the resonator changes in accordance with the changes in the load on the circuit.

Figure 5:
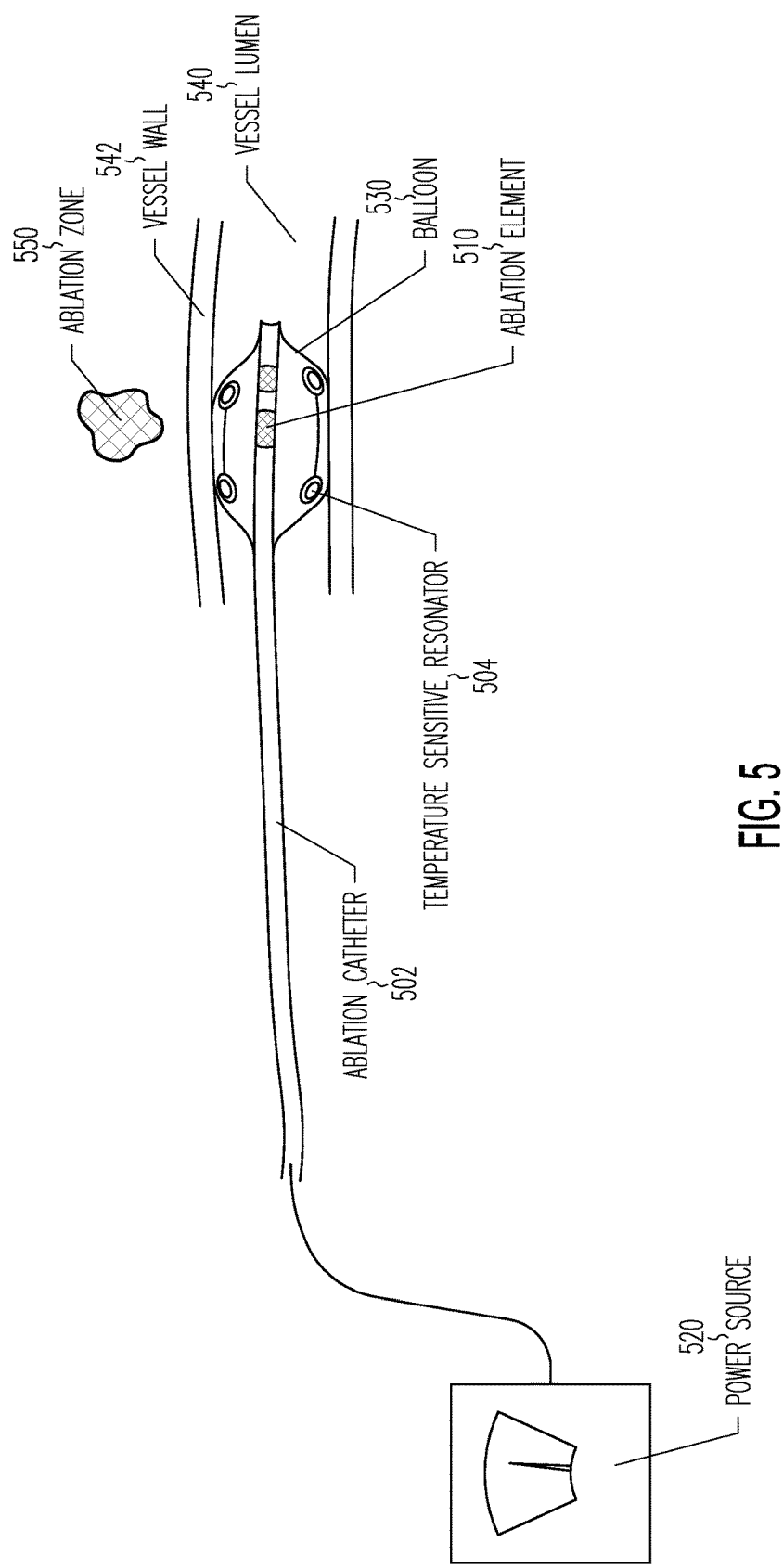
FIG. 5 illustrates an ablation catheter with wireless temperature sensors, according to various embodiments of the present subject matter.

FIG. 5 illustrates an ablation catheter with wireless temperature sensors, according to various embodiments of the present subject matter. The ablation catheter 502 enables real time temperature monitoring during therapy and includes at least one temperature sensitive resonator 504, which may or may not be directly connected or coupled to the catheter. The ablation catheter 502 is configured to have a portion, including an ablation element 510, be inserted into a vessel lumen 540 to ablate a target tissue volume 550 including the renal nerve beyond the vessel wall 542. In various embodiments, the system includes a balloon 530 configured to inflate to bring temperature sensitive resonator(s) 504 in proximity of the vessel wall 542. Energy for performing therapy is supplied to the ablation catheter 502 by an external electrical power source 520 while temperature monitoring functions are controlled by an external device (such as external device 602 in FIG. 6). The external device includes a transmit and receive antenna, control circuitry, and a display, in various embodiments. In some embodiments, the external electrical power supply 502 of the ablation catheter is also incorporated within the external device.

Figure 6:
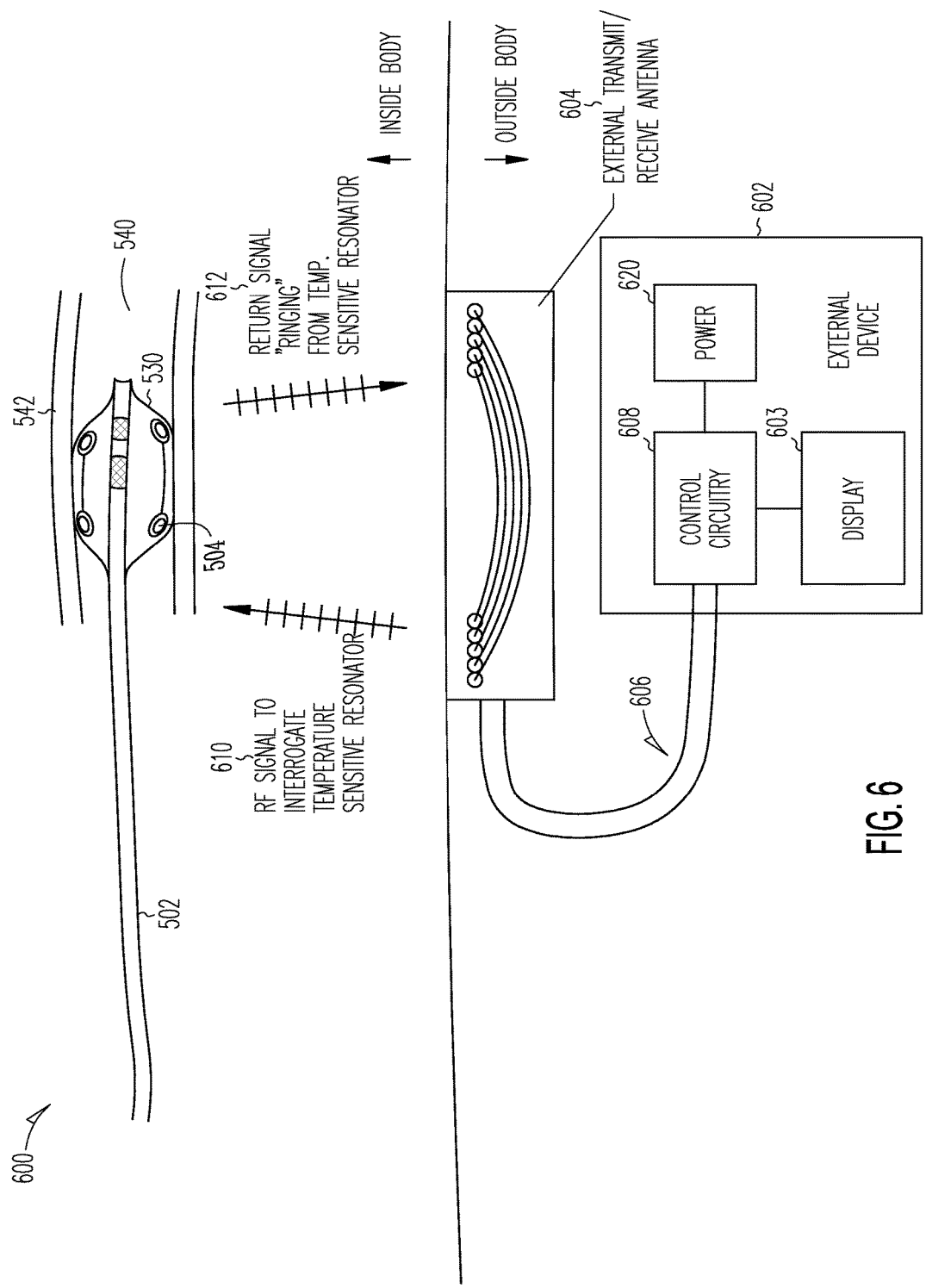
FIG. 6 illustrates an ablation catheter system with wireless temperature sensing, according to various embodiments of the present subject matter.

FIG. 6 illustrates an ablation catheter system with wireless temperature sensing, according to various embodiments of the present subject matter. An external device 602 is configured to generate a first signal 610 to interrogate the temperature sensitive resonator(s) 504, and is further configured to receive and decode a second signal 612 emitted from the temperature sensitive resonator(s) 504 in response to being interrogated. The first signal 610 and the second signal 612 are RF signals, in various embodiments. Other types of wireless signals can be used without departing from the scope of the present subject matter. In various embodiments, the external device 602 includes an external antenna 604 connected via wires 606 to the external device housing, the antenna 604 configured to transmit the first signal 610 and receive the second signal 612. In other embodiments, the external antenna 604 is a transducer capable of converting other forms of energy. In various embodiments, the external device 602 also includes a display 603 for communicating the sensed temperature information; circuitry 608 to control the sequence of temperature measurement, transmission, reception, and decoding; and a power supply 620. In other embodiments, the power supply 620 and circuitry 608 are used to control ablation therapy delivery. In some embodiments, the display 603 is connected to but separate from the external device 602.

The temperature sensitive resonator 504 transmits temperature data from the vicinity of the targeted treatment volume to the external device 602, in various embodiments. Once excited by external interrogation, the temperature sensitive resonator "rings" (resonates) at a frequency dependent on its temperature, thus transmits a signal with slightly different frequency as therapy progresses. Upon interrogating the resonator 504 to resonate, the external device 602 receives the signal emitted by the resonator 504, identifies the resonant frequency, and determines the corresponding tissue temperature. Thus the present subject matter provides real time, wireless temperature monitoring during the course of treatment. The passive temperature sensitive resonators 504 are compact and low cost.

In various embodiments, the ablation catheter delivers RF energy to induce tissue damage, for an application such as renal denervation. The ablation catheter delivers ultrasound or acoustic energy to induce tissue damage, in various other embodiments. The ablation catheter includes a balloon surrounding the ablation element, in various embodiments, the balloon contacting the vessel wall and having at least one temperature sensitive resonator disposed within the balloon to sense temperature in the proximity of the vessel wall. The balloon is irrigated with a solution of known temperature to establish a reference temperature for calibrating the temperature sensitive resonator(s), according to various embodiments. In various embodiments, multiple temperature sensitive resonators are coupled to the ablation catheter, each resonator designed to be centered about a different resonant frequency, allowing each to be uniquely identified and enabling multipoint temperature sensing. The external device for generating the interrogation signal and receiving and decoding the temperature signal is reusable, in various embodiments.

FIG. 7 illustrates a flow diagram of a method of using an ablation catheter system with wireless temperature sensing, according to various embodiments of the present subject matter. In various embodiments, an external device sends an RF signal to excite the temperature sensitive resonator, at 701. The resonator resonates or "rings" in response to the external excitation, emitting a signal with frequency related to the temperature of the resonator. The external device, with receive capability, receives the "ringing" from the temperature sensitive resonator which is disposed upon the ablation catheter, at 702. At 703, the external device identifies the frequency of the ringing and determines a temperature (or temperature change) associated with the signal frequency. The temperature information is transmitted to a real time display at 704, in various embodiments.

Other types of wireless signals can be used without departing from the scope of the present matter. In some embodiments, acoustic signals are transmitted and received in place of RF signals. In some embodiments, surface acoustic wave or bulk acoustic wave sensors may be applied in place of electrical resonators. In other embodiments, piezoelectric transducers harvest acoustic energy and emit an acoustic signal.

One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. For example, the present subject matter can be applied to other medical procedures where heating or ablation of tissue is desired. The scope of the present subject matter should be determined with reference to the appended claims, along with the full scope of legal equivalents to which such claims are entitled.

What is claimed is:

1. An ablation catheter system, comprising:
   an ablation catheter;
   at least one temperature sensitive resonator coupled to the ablation catheter, the at least one temperature sensitive resonator configured to be placed proximate to and in thermal conduction with a target zone of tissue and to resonate at a resonance frequency that depends upon a temperature sensed by the at least one temperature sensitive resonator; and
   an external device configured to generate a wireless first radio frequency (RF) signal to interrogate the at least one temperature sensitive resonator and to receive and decode a wireless second RF signal from the at least one temperature sensitive resonator in response to being interrogated, the wireless second RF signal indicative of the temperature sensed by the at least one temperature sensitive resonator.

2. The system of claim 1, further comprising a balloon coupled to the ablation catheter, the balloon configured to be inflated to cause a balloon wall to contact a vessel wall, wherein the at least one temperature sensitive resonator is disposed within the balloon wall.

3. The system of claim 1, comprising multiple at least one temperature sensitive resonators coupled to the ablation catheter, each temperature sensitive resonator configured to resonate at a different resonance frequency range allowing each to be uniquely identified and enabling multipoint temperature sensing.

4. The system of claim 1, wherein the ablation catheter is configured to deliver RF energy to induce tissue damage for a therapeutic ablation procedure.

5. The system of claim 1, wherein the ablation catheter is configured to deliver ultrasonic energy to induce tissue damage for a therapeutic ablation procedure.

6. The system of claim 1, wherein the ablation catheter is configured to be inserted in a renal artery and to provide ablation therapy to a renal nerve to treat hypertension.

7. A method of using the ablation catheter system of claim 1, the method comprising:
   delivering electrical power, using an external electrical generator, to the ablation catheter to provide an ablation therapy to the target zone of tissue;
   applying the wireless first RF signal to interrogate the at least one temperature sensitive resonator coupled to the ablation catheter, including:
   exciting the at least one temperature sensitive resonator to emit the wireless second RF signal in response to the wireless first RF signal; and
   receiving and decoding the wireless second RF signal to determine a temperature for the target zone of tissue using the wireless second RF signal.

8. The method of claim 7, wherein applying a wireless first RF signal to interrogate the resonator includes wirelessly interrogating a loop coil resonator.

9. The method of claim 8, wherein the loop coil resonator is patterned on a substrate of a polymeric balloon.

10. The method of claim 7, further comprising transmitting the determined temperature to a real time display.

11. The system of claim 1, wherein the at least one temperature sensitive resonator includes a temperature sensitive resistor or a temperature sensitive capacitor.

12. The system of claim 1, wherein the at least one temperature sensitive resonator includes an inductor, a capacitor and a temperature sensitive resistor.

* * * * *